| United States Patent [19] | [11] 4,016,197 |
| --- | --- |
| Baiocchi | [45] Apr. 5, 1977 |

[54] 4-ACETAMIDOPHENYL-P-ISOBUTYL HYDRATROPATE

[75] Inventor: Leandro Baiocchi, Rome, Italy

[73] Assignee: Aziende Chimiche Riunite Angelini Francesco A.C.R.A.F. S.p.A., Italy

[22] Filed: May 1, 1975

[21] Appl. No.: 573,410

[30] Foreign Application Priority Data

May 15, 1974 Italy .................................. 51002/74

[52] U.S. Cl. ............................. 260/477; 424/308
[51] Int. Cl.$^2$ ....................................... C07C 69/76
[58] Field of Search .................................. 260/477

[56] References Cited

UNITED STATES PATENTS 3,481,972  12/1969  Trepanier ..................... 260/477

OTHER PUBLICATIONS

Fieser et al., *Reagents for Organic Synthesis*, pp. 232, 233, 876, 877, 1179, 1183, 1184 (1967).
Morrison et al., *Organic Chemistry*, 3rd Ed. p. 602 (1973).
Julia et al., as cited in C.A. 47, 3815 (1952).

*Primary Examiner*—Jane S. Myers
*Attorney, Agent, or Firm*—Robert E. Burns; Emmanuel J. Lobato; Bruce L. Adams

[57] ABSTRACT

4-Acetamidophenyl-p-isobutyl hydratropate having analgesic, anti-inflammatory, antipyretic and antirheumatic activity.

1 Claim, No Drawings

4-ACETAMIDOPHENYL-P-ISOBUTYL HYDRATROPATE

This invention relates to 4-acetamidophenyl p-isobutyl-hydratropate (I)

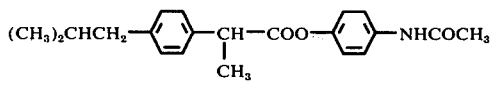

and a method of preparing the same.

This product (I) is a substance or material having analgesic, anti-inflammatory, antipyretic and antirheumatic activity on laboratory animals. In view of its poor toxicity and extended spectrum of useful pharmacologic actions, the use of such a substance in human therapy can be foreseen for many affections, such as from influenza to the most serious rheumatic diseases, at daily doses in the range of 0.8–2.5 g.

According to the present invention, product (I) is prepared from p-isobutyl-hydratropic acid by reacting with p-acetylaminophenol, in the presence of an acidic chloride, such as for example $POCl_3$, or p-toluen-sulphochloride, or other condensing agent, such as for example di-cyclohexyl-carbo-diimide. It may be also convenient to convert first p-isobutylhydratropic acid into the corresponding chloride, for example through the action of $SOCl_2$, and then without any purification, reacting the latter with p-acetylaminophenol.

Some unrestrictive examples will now be given in the following in order to illustrate the method according to the present invention.

EXAMPLE 1

A mixture comprising 2 g. p-isobutyl-hydratropic acid, 1.5 g. p-acetylaminophenol and 1 cc. phosphorous oxychloride was heated at 80° C for 2 hours. The mixture was cooled and the residue distempered in 2N sodium carbonate solution and extracted with ether. The ether extracts were washed with water, dried on sodium sulphate and vacuum concentrated. The residue was crystallized from cyclohexane. 2 g. microcrystalline solid were obtained, m.p. 89°–90° C.

This substance showed analytic values and NMR spectrum in accordance with formula $C_{21}H_{25}NO_3$ and was unique on thin layer: Kieselgel Merck F 254, benzol-ether eluent 1:1 Rf = 0.2 riv. UV lamp and iodine vapours.

EXAMPLE 2

A solution of 2 g. p-isobutyl-hydratropic acid, 1.5 g. p-acetylaminophenol, 3.6 g. p-toluensulphochloride in 20 cc. pyrridine was stirred in water and ice bath for 3 hours. The solution was then poured in cold water, separated oil was extracted, the ether extracts were washed with water, diluted HCl, water, 2N sodium carbonate solution and water, dried on sodium sulphate and vacuum concentrated. The residue (3.5 g.) was crystallized from cyclohexanebenzol 9:1.

EXAMPLE 3

A solution of 2 g. p-isobutyl-hydratropic acid and 1.5 g. p-acetylaminophenol in 50 cc. anhydrous tetrahydrofuran was added under cooling with ice and stirring with 2 g. N,N-dicyclohexyl-carbo-di-imide. The initially clear solution became turbid as dicyclohexyl-urea was separated. After 3 hours, the tetrahydrofuran solution was filtered, concentrated under reduced pressure, the residue was distempered in water, extracted with ether, the ether extracts were washed with 2 N sodium carbonate solution and water, dried on sodium sulphate and concentrated under reduced pressure. 2.7 g. self-solidifing oleous residue were obtained. The product was crystallized from cyclohexanebenzol 9:1, m.p. 89°–90° C.

EXAMPLE 4

3.5 g. (2.1 cc.) thionyl chloride were added to 5 g. p-isobutyl-hydratropic acid dissolved in 25 cc. anhydrous benzol. The solution was heated under stirring until completed development of HCl, then cooled, vacuum concentrated and taking up with toluene to remove the residual traces of chlorinating agent. The oleous residue (5.7 g.) was dissolved in 50 cc. anhydrous dioxane, the adding 2 cc. pyridine and under stirring 3.65 g. p-acetylaminophenol. The mixture was left under stirring at room temperature for 24 hours. The mixture was then poured in water, the separated oil was extracted with ether, and the extracted ethers were washed with 2N sodium carbonate solution, water, diluted HCl, water, saturated bicarbonate solution, and again water. The product was dried on $Na_2SO_4$ and concentrated under reduced pressure: a dense self-solidifying oleous residue was obtained. The residue was crystallized from cyclohexane, thus obtaining 5 g. pure product, m.p. 89°–90° C.

What is claimed is :

1. 4-acetamidophenyl-p-isobutyl hydrotropate (m.p. 89°–90° C) of the formula:

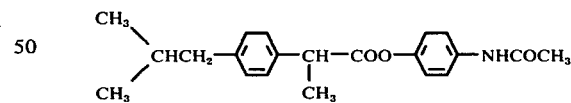

* * * * *